(12) United States Patent
Van Broekhoven et al.

(10) Patent No.: US 8,163,969 B2
(45) Date of Patent: *Apr. 24, 2012

(54) ALKYLATION PROCESS USING A CATALYST COMPRISING RARE EARTH CONTAINING ZEOLITES AND A HYDROGENATION METAL

(75) Inventors: Emanuel Hermanus Van Broekhoven, Monnickendam (NL); Mark Hendrikus Harte, Zaandam (NL); Gijsbertus Klaver, Ilpendam (NL); Jan Nieman, Maarssen (NL)

(73) Assignee: Albemarle Netherlands B.V., Amsterdam (NL)

( * ) Notice: Subject to any disclaimer, the term of this patent is extended or adjusted under 35 U.S.C. 154(b) by 1106 days.

This patent is subject to a terminal disclaimer.

(21) Appl. No.: 12/021,096

(22) Filed: Jan. 28, 2008

(65) Prior Publication Data
US 2008/0183025 A1      Jul. 31, 2008

Related U.S. Application Data

(60) Provisional application No. 60/898,039, filed on Jan. 26, 2007.

(51) Int. Cl.
*C07C 2/58* (2006.01)
*C07C 2/54* (2006.01)
(52) U.S. Cl. ............................. 585/722; 585/710
(58) Field of Classification Search ............ 585/722, 585/710
See application file for complete search history.

(56) References Cited

U.S. PATENT DOCUMENTS 3,851,004 A * 11/1974 Chang-lee Yang ............ 585/467
4,918,255 A * 4/1990 Chou et al. .................... 585/331

FOREIGN PATENT DOCUMENTS
WO    98/23560    6/1998

* cited by examiner

*Primary Examiner* — Thuan Dinh Dang
(74) *Attorney, Agent, or Firm* — Jeremy J. Kliebert

(57) ABSTRACT

An improved alkylation process utilizing a solid-acid catalyst comprising a rare earth containing zeolite and a hydrogenation metal is disclosed.

32 Claims, 3 Drawing Sheets

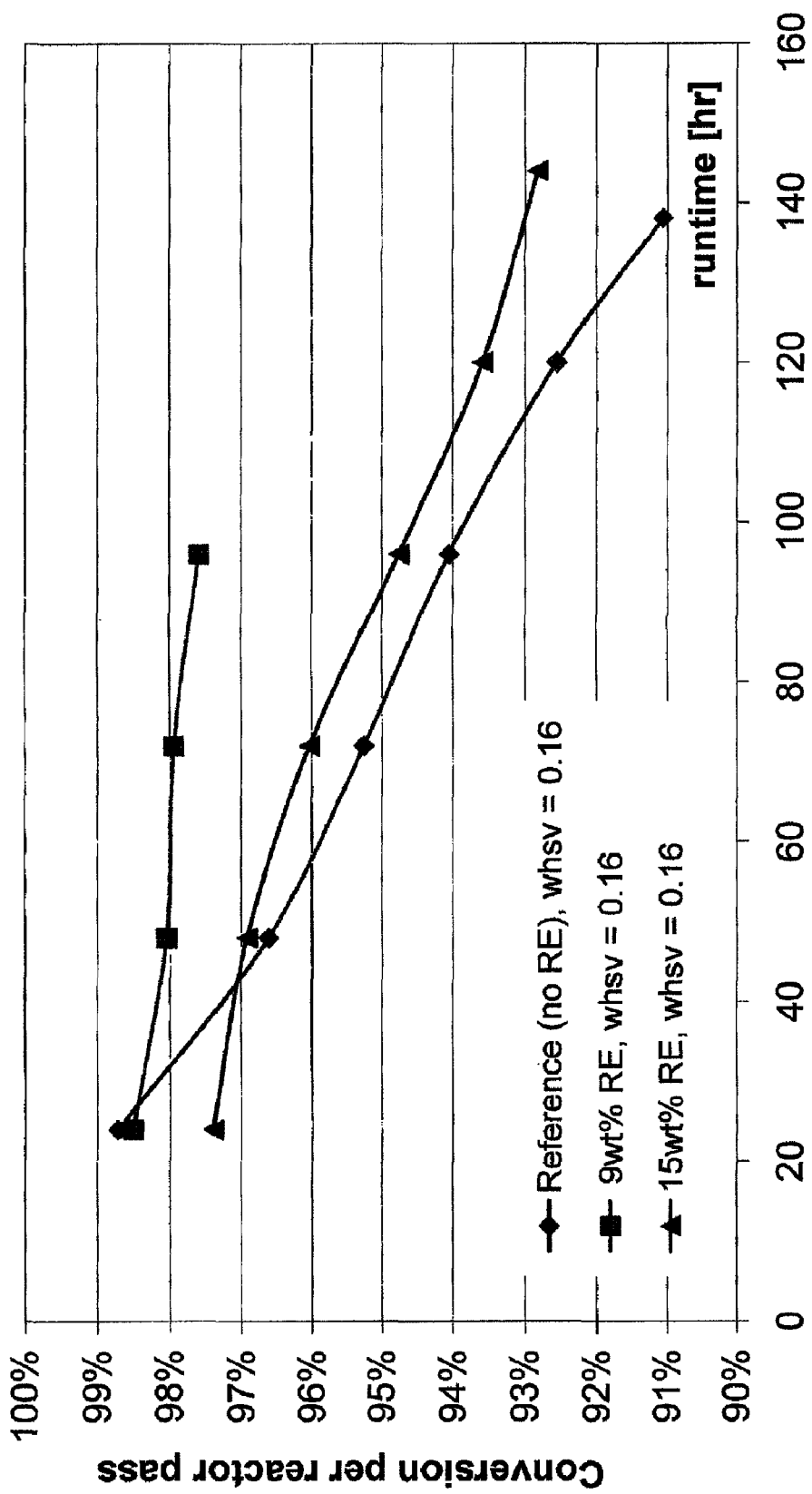

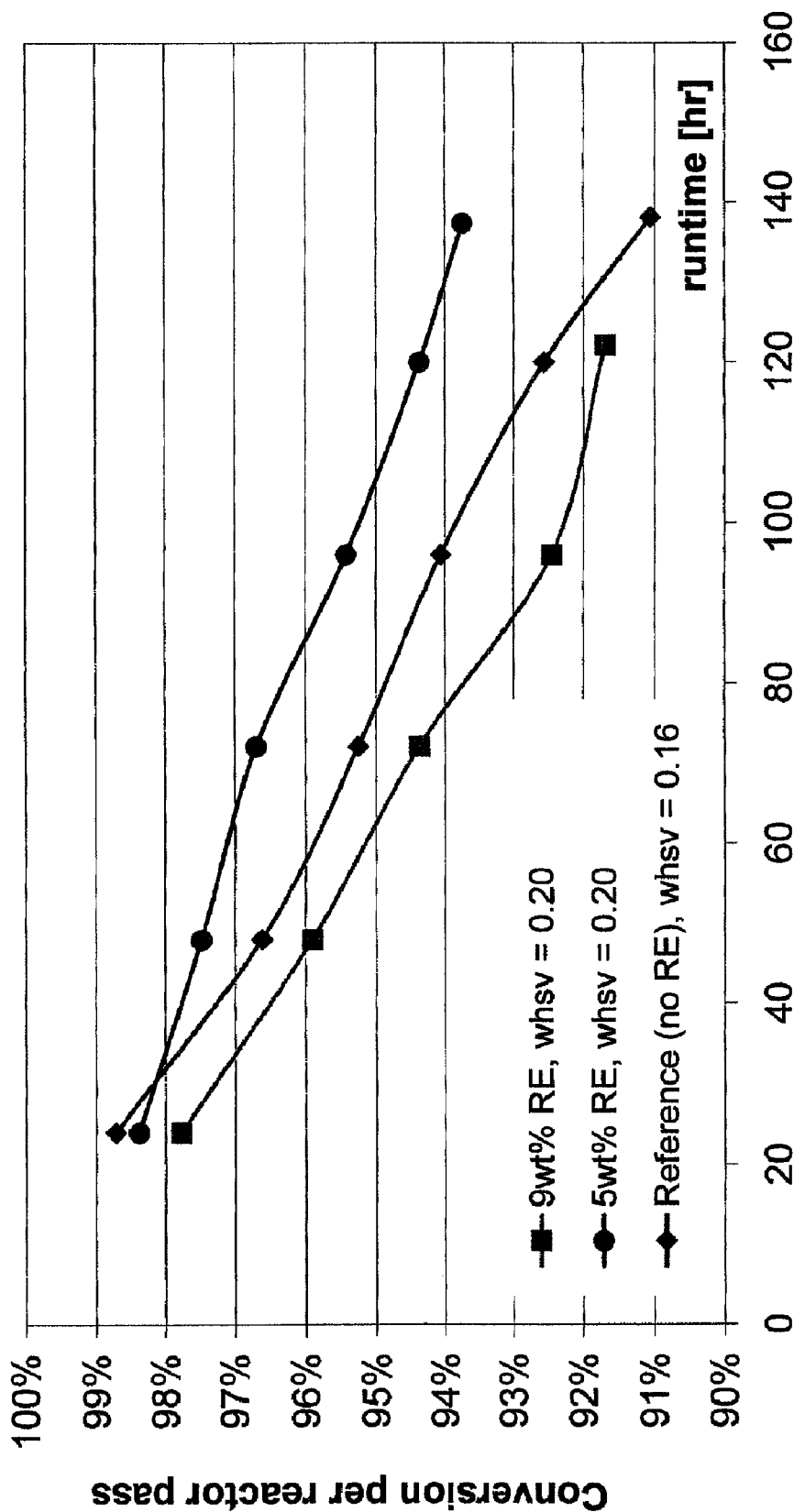

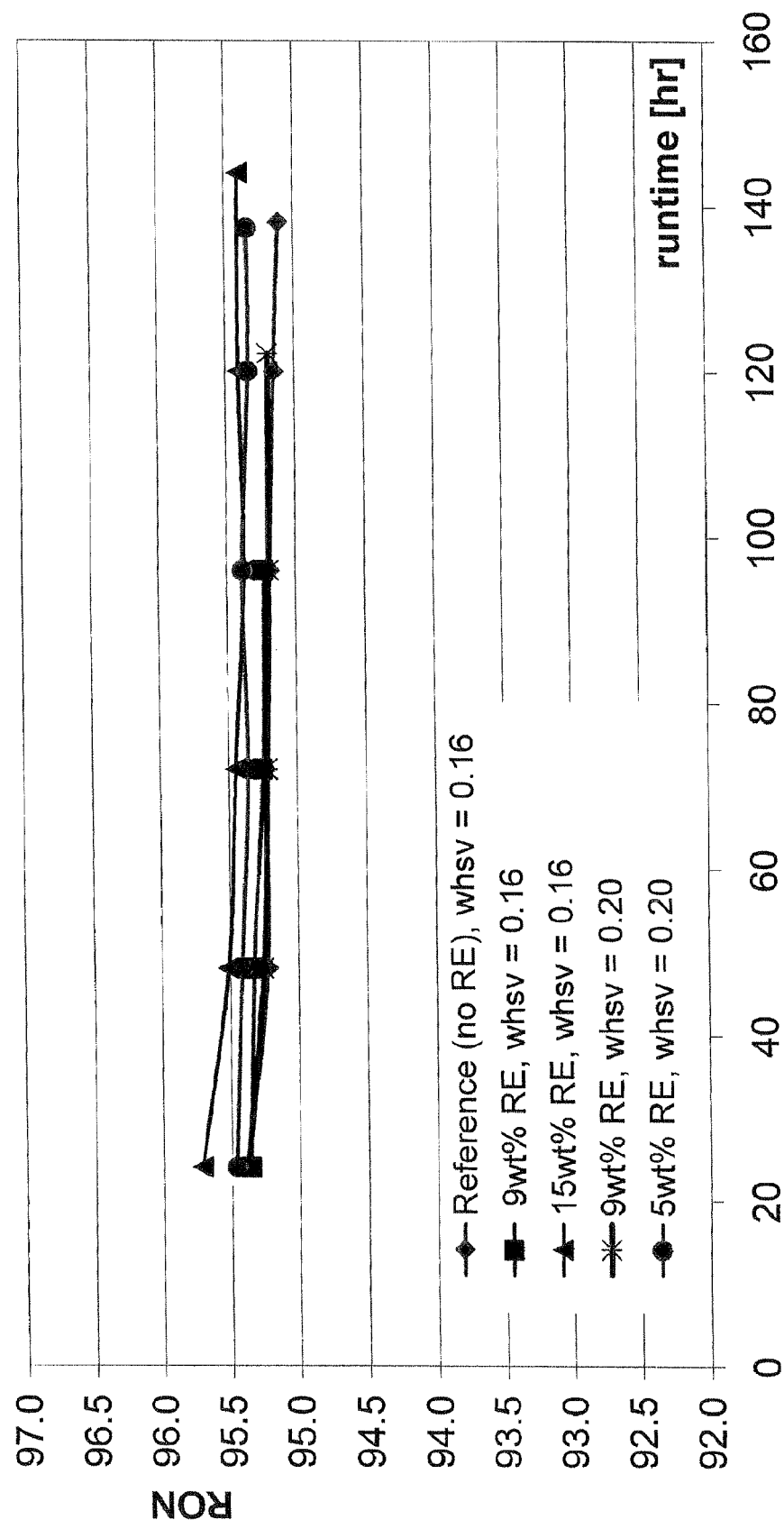

ALKYLATION PROCESS USING A CATALYST COMPRISING RARE EARTH CONTAINING ZEOLITES AND A HYDROGENATION METAL

The term alkylation refers to the reaction of an alkylatable compound, such as an aromatic or saturated hydrocarbon, with an alkylation agent, such as an olefin. The reaction is of interest because it makes it possible to obtain, through the alkylation of isobutane with an olefin containing 2-6 carbon atoms, an alkylate which has a high octane number and which boils in the gasoline range. Unlike gasoline obtained by cracking heavier petroleum fractions such as vacuum gas oil and atmospheric residue, gasoline obtained by alkylation is essentially free of contaminants such as sulfur and nitrogen and thus has clean burning characteristics. Its high anti-knock properties, represented by the high octane number, lessen the need to add environmentally harmful anti-knock compounds such as aromatics or lead. Also, unlike gasoline obtained by reforming naphtha or by cracking heavier petroleum fractions, alkylate contains few if any aromatics or olefins, which offers further environmental advantages.

The alkylation reaction is acid-catalyzed. Conventional alkylation process equipment makes use of liquid acid catalysts such as sulfuric acid and hydrofluoric acid. The use of such liquid acid catalysts is attended with a wide range of problems. For instance, sulfuric acid and hydrofluoric acid are both highly corrosive, so that the equipment used has to meet severe service requirements. Since the presence of highly corrosive materials in the resulting fuel is objectionable, the remaining acid must be removed from the alkylate. Also, because of the liquid phase separations that must be carried out, the process is complicated and expensive. In addition, there is always the risk that toxic substances such as hydrogen fluoride will be emitted to the environment.

The present invention provides an improved alkylation process utilizing a solid-acid catalyst comprising a rare earth containing zeolite and a hydrogenation metal.

The water content of the catalyst ranges from about 1.5 wt % to about 6 wt %, in one embodiment it ranges from about 1.8 wt % to about 4 wt %, and in another embodiment it ranges from about 2 wt % to about 3 wt %. The water content of the catalyst is defined as its water content during use in the alkylation process and is measured by determining the weight loss upon heating the catalyst for two hours at 600° C. (Loss on Ignition, or LOI 600).

The catalyst further comprises a hydrogenation metal. Examples of suitable hydrogenation metals are the transition metals, such as metals of Group VIII of the Periodic Table, and mixtures thereof. Among these, noble metals of Group VIII of the Periodic Table are preferred. Platinum, palladium, and mixtures thereof are especially preferred. The amount of hydrogenation metal will depend on its nature. When the hydrogenation metal is a noble metal of Group VIII of the Periodic Table, the catalyst generally will contain in the range of about 0.01 to about 2 wt % of the metal. In one embodiment it ranges from about 0.1 to about 1 wt %, calculated as metal and based on the total weight of the catalyst.

The catalyst further comprises a solid acid. Examples of solid acids are zeolites such as zeolite beta, MCM-22, MCM-36, mordenite, faujasites such as X-zeolites and Y-zeolites, including H—Y-zeolites and USY-zeolites, non-zeolitic solid acids such as silica-alumina, sulfated oxides such as sulfated oxides of zirconium, titanium, or tin, mixed oxides of zirconium, molybdenum, tungsten, phosphorus, etc., and chlorinated aluminium oxides or clays. Preferred solid acids are zeolites, including mordenite, zeolite beta, faujasites such as X-zeolites and Y-zeolites, including HY-zeolites and USY-zeolites. Mixtures of solid acids can also be employed. In one embodiment the solid acid is a faujasite with a unit cell size ($a_0$) of 24.72 to about 25.00 angstroms, in another embodiment the solid acid is Y-zeolite with a unit cell size of 24.34-24.72 angstroms, while in another the solid acid is Y-zeolite with a unit cell size of 24.42-24.56 angstroms. In yet another embodiment the solid acid is Y-zeolite with a unit cell size of 24.56-24.72 angstroms.

The solid acid component of the catalyst comprises rare earth, i.e., an element chosen from the lanthanide series. In one embodiment, rare earth ranges from about 0.5 wt % to about 32 wt %. In another, rare earth ranges from about 2 wt % to about 9 wt %. In yet another, rare earth ranges from about 4 wt % to about 6 wt %. All references herein to rare earth wt % are calculated as rare earth oxides on a dry basis (600° C., 1 hour).

The rare earth element(s) may be exchanged into the solid acid component by conventional means. In one embodiment, the solid acid component is a lanthanum exchanged Y-zeolite.

During the exchange process of the solid acid component sodium ($Na^+$) is removed from the catalyst. In one embodiment the solid acid component contains less than 1.5 wt % $Na_2O$. In another, less than 1.0 wt % $Na_2O$. In yet another less than 0.6 wt % $Na_2O$, all calculated on dry basis (600° C., 1 hour).

The catalyst may additionally comprise a matrix material. Examples of suitable matrix materials are alumina, silica, titania, zirconia, clays, and mixtures thereof. Matrix materials comprising alumina are generally preferred. In one embodiment, the catalyst comprises about 2 wt % to about 98 wt % of the solid acid and about 98 wt % to about 2 wt % of the matrix material, based on the total weight of the solid acid and the matrix material present in the catalyst. In another embodiment, the catalyst comprises about 10 wt % to about 90 wt % of the solid acid and about 90 wt % to about 10 wt % of the matrix material, based on the total weight of the solid acid and the matrix material contained in the catalyst. In another embodiment, the catalyst comprises about 10 wt % to about 80 wt % of matrix material and balance solid acid. In yet another embodiment, the catalyst comprises about 10 wt % to about 40 wt % of the matrix material and balance solid acid, based on the total weight of the solid acid and the matrix material contained in the catalyst.

The catalyst preferably contains no halogen component.

In one embodiment, the catalyst comprises catalyst particles wherein the ratio between (i) the volume in catalyst pores with a diameter of about 40 to about 8,000 nm (herein defined as "macropores") and (ii) the specific length of the catalyst particles is in the range of about 0.01 to about 0.90 ml/(g*mm), and wherein the catalyst has a total pore volume of at least 0.20 ml/g.

The specific length of a catalyst particle is defined as the ratio between the geometric volume and the geometric surface of the solid part of this catalyst particle. The determination of the geometric volume and the geometric surface is known to the person skilled in the art and can be carried out, e.g., as described in DE 2354558.

The macropore volume as well as the total pore volume is determined via mercury intrusion on the basis of the Washburn equation covering pores with a diameter of 3.6-8,000 nm.

In one embodiment, the ratio between the volume in macropores and the specific length is above about 0.20 ml/(g*mm), and in another above about 0.30 ml/(g*mm). In yet another embodiment, the ratio is above about 0.40 ml/(g*mm), but below about 0.80 ml/(g*mm).

In one embodiment, the catalyst has a total pore volume of at least about 0.23 ml/g and in another at least about 0.25 ml/g.

In one embodiment, the catalyst particles have a specific length of at least about 0.10 mm, in another at least about 0.16 mm, and in yet another at least about 0.20 mm. In one embodiment, the upper limit of the specific length lies at about 2.0 mm, in another at about 1.0 mm, and in yet another at about 0.6 mm.

The pore volume in macropores in one embodiment of the catalyst is at least about 0.05 ml/g, in another at least about 0.08 ml/g. In one embodiment, the upper limit of the pore volume in macropores is below about 0.30 ml/g, in another below about 0.25 ml/g.

The particles of the catalyst can have many different shapes, including spheres, cylinders, rings, and symmetric or asymmetric polylobes, for instance tri- and quadrulobes.

In one embodiment, the catalyst particles have an average particle diameter of at least about 0.5 mm, in another embodiment at least about 0.8 mm, and in yet another embodiment at least about 1.0 mm. In one embodiment, the upper limit of the average particle diameter lies at about 10.0 mm, in another at about 5.0 mm, and in yet another embodiment at about 3.0 mm.

The catalyst used in the process according to the invention is prepared by adjusting the water content. For example, the solid acid constituent may be mixed with a matrix material, to form carrier particles, followed by calcination of the particles. The hydrogenating function may, e.g., be incorporated into the catalyst composition by impregnating the carrier particles with a solution of a hydrogenation metal component. After impregnation the catalyst may be calcined.

In one embodiment, the catalyst is reduced at a temperature in the range of about 200 to about 500° C. in a reducing gas such as hydrogen. In another embodiment, the catalyst is reduced at a temperature in the range of about 250 to about 350° C. The reduction can be performed before adjustment of the water content, after addition of water to the catalyst and/or by using reduction as a way to adjust the water content. In one embodiment, the reduction is performed before adjustment of the water content. In another, the reduction is performed after drying the catalyst in a dry, non-reducing gas (such as nitrogen, helium, air, and the like).

The water content of the catalyst can be adjusted by various methods as described in PCT/EP2005/000929, which is incorporated by reference in its entirety. Such methods are exemplified below as methods 1, 2, and 3.

Method 1 involves increasing the LOI of a catalyst by exposing the catalyst to water. This can be achieved by exposing the catalyst to a water-containing atmosphere, e.g., air at ambient conditions. Embodiments of this method include exposing a reduced catalyst to water until the desired LOI is reached, exposing an unreduced catalyst to water until an LOI above the desired level is reached, followed by reduction of the catalyst, thereby decreasing the LOI to the desired level, exposing a reduced catalyst to water until an LOI above the desired level is reached, followed by treatment of the catalyst in either an inert or a reducing atmosphere, thereby decreasing the LOI to the desired level, and reducing the catalyst in a hydrogen and water-containing atmosphere.

Method 2 involves decreasing the LOI of an existing catalyst to the desired level by reducing an unreduced catalyst with an LOI above the desired level.

Method 3 involves in-situ water addition by starting the alkylation process with a catalyst having an LOI below the desired level and adding water to the alkylation unit during processing, for instance by adding water to the hydrocarbon feed, by regenerating the catalyst in a water-containing atmosphere and/or by exposing the regenerated catalyst to a water-containing atmosphere.

A combination of two or more of the above methods may also be employed.

The hydrocarbon to be alkylated in the alkylation process is a branched saturated hydrocarbon such as an isoalkane having 4-10 carbon atoms. Examples are isobutane, isopentane, isohexane or mixtures thereof. The alkylation agent is an olefin or mixture of olefins having 2-10 carbon atoms. In one embodiment, the alkylation process consists of the alkylation of isobutane with butenes.

As will be evident to the skilled person, the alkylation process can take any suitable form, including fluidized bed processes, slurry processes, and fixed bed processes. The process can be carried out in a number of beds and/or reactors, each with separate addition of alkylation agent if desirable. In such a case, the process of the invention can be carried out in each separate bed or reactor.

As mentioned above, water may be added during the process in order to increase the LOI of the catalyst to the desired level. This water can be introduced during the alkylation reaction via, e.g., the hydrocarbon feed or the feed of alkylation agent. Alternatively, the catalyst can be hydrated by using a water-containing atmosphere during the optional (mild) regeneration steps described below, or by contacting the catalyst with water in a separate intermediate hydration step. Similar procedures can be applied to rehydrate the catalyst after its LOI has decreased during processing (i.e. during the alkylation reaction and/or regeneration).

Suitable process conditions are known to the skilled person. Preferably, an alkylation process as disclosed in WO 98/23560 is applied. The process conditions applied in the present process are summarized in the following Table:

|  | Temperature range [° C.] | Pressure range [bar] | Molar ratio of hydrocarbon to alkylation agent |
| --- | --- | --- | --- |
| Preferred | −40-250 | 1-100 | 5:1-5,000:1 |
| More preferred | 20-150 | 5-40 | 50:1-1,000:1 |
| Most preferred | 65-95 | 15-30 | 150:1-750:1 |

Optionally, the catalyst may be subjected to high-temperature regeneration with hydrogen in the gas phase. This high-temperature regeneration may be carried out at a temperature of at least about 150° C., in one embodiment regeneration is carried out at about 150° to about 600° C., and another at about 200° to about 400° C. For details of this regeneration procedure, reference is made to WO 98/23560, and in particular to page 4, lines 12-19, which is herein incorporated in its entirety by reference. The high-temperature regeneration can be applied periodically during the alkylation process. If as a result of high-temperature regeneration the water content of the catalyst has decreased to below the desired level, the catalyst may be rehydrated during the process in the ways described above.

In addition to the high-temperature regeneration treatment, a milder regeneration may be applied during the alkylation process, such as described in WO 98/23560, in particular page 9, line 13 through page 13, line 2, which is herein incorporated in its entirety by reference. During the alkylation process, the catalyst may be subjected intermittently to a regeneration step by being contacted with a feed containing a hydrocarbon and hydrogen, with said regeneration being carried out at about 90% or less of the active cycle of the catalyst in one embodiment, at 60% or less in another embodiment, at 20% or less in yet another embodiment, and at 10% or less in another embodiment. The active cycle of the catalyst is defined herein as the time from the start of the feeding of the alkylation agent to the moment when, in comparison with the alkylation agent added to the catalyst-containing reactor section, 20% of the alkylation agent leaves the catalyst-containing reactor section without being converted, not counting isomerization inside the molecule.

The preparation of a catalyst of the present invention comprises the steps of: a) calcining solid acid-containing particles at a temperature in the range of about 400 to about 575° C.; b) incorporating a Group VIII noble metal into the calcined particles to form noble metal-containing particles; and c) calcining the noble metal-containing particles at a temperature in the range of about 350 to about 600° C.

Performance in alkylation reactions of catalysts of the present invention can be further improved if the calcination steps before and after incorporation of the hydrogenation component are both conducted in a specific temperature window.

The solid acid-containing particles are calcined in step a) at a temperature in the range of about 400 to about 575° C., in another embodiment in the range of about 450 to about 550° C., and in yet another embodiment in the range of about 460 to about 500° C. The heating rate ranges from about 0.1 to about 100° C./min, and in one embodiment from about 0.5° C. to about 50° C./min, and in another embodiment from about 1 to about 30° C./min. Calcination is conducted for about 0.01 to about 10 hrs, and in one embodiment for about 0.1 to about 5 hrs, and in another embodiment for about 0.5 to about 2 hrs. It may be conducted in an air and/or inert gas (e.g. nitrogen) flow. In one embodiment this gas flow is dry.

In another embodiment, the solid acid-containing particles are dried before being calcined. This drying may be conducted at a temperature of about 110 to about 150° C.

The calcination can be performed in any equipment, such as a fixed bed reactor, a fluidized bed calciner, and a rotating tube calciner.

A Group VIII noble metal is then incorporated into the calcined solid acid-containing particles in step b). In one embodiment, this is preformed by impregnation or competitive ion exchange of the solid acid-containing particles using a solution comprising Group VIII noble metal ions and/or their complexes and (optionally) NH4+ ions. In another embodiment, the Group VIII noble metals are platinum, palladium, and combinations thereof. In yet another embodiment, at least one of the Group VIII noble metals is platinum. Suitable Group VIII noble metal salts include nitrates, chlorides, and ammonium nitrates of the noble metals or their complexes (e.g. NH3 complexes).

The resulting noble metal-containing particles are then calcined at a temperature in the range of 350-600° C. in step c). In one embodiment, the particles are calcined at about 400 to about 550° C., and in another from about 450 to about 500° C. This temperature is may be reached by heating the particles by about 0.1 to about 100° C./min to the desired final value between about 350 and about 600° C. In one embodiment, they are heated by about 0.5 to about 50° C./min, in another by about 1 to about 30° C./min. Calcination may be conducted for about 0.01 to about 10 hrs, and in one embodiment for about 0.1 to about 5 hrs, and in another for about 0.5 to about 2 hrs. Calcination may be conducted in an air and/or inert gas (e.g. nitrogen) flow. In one embodiment this gas flow is dry.

Optionally, a separate drying step is applied between steps (b) and (c). Alternatively, the noble metal-containing particles are dried during the calcination step. Also optionally, a dwell of about 15-120 minutes is introduced at a temperature of about 200 to about 250° C.

After calcination step (c), the resulting catalyst particles may be reduced at a temperature range of about 200 to about 500° C., in one embodiment from about 250 to about 350° C., in a reducing gas such as hydrogen.

EXAMPLES

Performance of Catalyst Comprising Rare Earth Ions Compared to Reference Catalyst without Rare Earth (RE) Ions:

The reference standard Y-zeolite without rare earth ions was prepared via a conventional route, i.e., sodium-Y-zeolite (NaY) was prepared (SAR 5.5) followed by ion exchange with $NH_4^+$-ions (remaining $Na_2O$ typically about 4 wt %), steaming at about 575 to about 625° C. resulting in an $a_0$ of about 24.53-24.57 Å, a second ion exchange with $NH_4^+$-ions (remaining $Na_2O$ typically 1 wt %), further steaming at about 500 to about 550° C. resulting in an $a_0$ of about 24.44-24.52 Å, acid leaching with either $H_2SO_4$ or HCl at a temperature of about 80° C. to increase the bulk-SAR (SAR is defined as the ratio of SiO2 and Al2O3 (mol/mol) present in the zeolite material) from about 6 to about 12 ($Na_2O$ typically drops to about 0.2 wt %), and drying.

Zeolite of the invention are prepared according to similar procedures using the same starting materials, however $NH_4^+$- as well as rare earth ions are used in the first exchange step and the steaming temperature is about 400 to about 500° C. At this low steaming temperature, less non-framework alumina is formed and acid leaching is not required. So after the first steam treatment, only exchange with $NH_4^+$-ions is required and then the zeolite is dried. However, multiple steaming and ion exchange with $NH_4^+$-ions steps may be employed if required to achieve appropriate $a_0$ and $Na_2O$ content. In one embodiment, $Na_2O$ ranges from about 0.2 to about 1 wt %, $a_0$ ranges from about 24.58-24.68 angstrom and rare earth ranges from about 2 to about 9 wt %.

In another embodiment, $Na_2O$ content is lower than about 0.7 wt %, $a_0$ ranges from about 24.60-24.66 angstrom and rare earth ranges from about 4 to about 6 wt %.

Also a zeolite with about 15 wt % rare earth was prepared. In this case the procedure of the invention was followed but no NH4+ ions were added in the first exchange step.

The tested alkylation catalysts had the following compositions and properties: from about 60 to about 80% of the above-described zeolite, from about 20 to about 40% alumina, from about 0.15 to about 0.5% platinum, the average particle length ranges from about 2 to about 6 mm, the average length/diameter ratio ranges from about 1 to about 7.5, the particle diameter ranges from about 0.5 to about 3 mm, and the side crush strength ranges from about 1.5 to about 10 lbs/mm.

General Test Procedure:

A fixed-bed recycle reactor as described in WO 9823560, which is herein incorporated by reference in its entirety, having a diameter of 2 cm was filled with a 1:1 volume/volume mixture of 38.6 grams of catalyst extrudates (on dry basis, i.e. the actual weight corrected for the water content) and carborundum particles (60 mesh). At the center of the reactor tube a thermocouple of 6 mm in diameter was arranged. The reactor was flushed with dry nitrogen for 30 minutes (21 Nl/hour). Next, the system was tested for leakages at elevated pressure, after which the pressure was set to 21 bar and the nitrogen flow to 21 Nl/hour. The reactor temperature was then raised to 275° C. at a rate of 1° C./min, at 275° C. nitrogen was replaced by dry hydrogen and the catalyst was reduced at 275° C.

Alternatively, in case of high temperature regeneration of the same catalyst sample between runs, after draining and flushing the reactor with hydrogen to remove hydrocarbons while maintaining the alkylation reaction temperature, hydrogen flow was set to 21 Nl/hour and the reactor temperature was then raised to 275° C. at a rate of 1° C./min, and the catalyst was regenerated at 275° C.

After 2 hours, the reactor temperature was lowered to the reaction temperature of about 75° C. During cooling down water was added to the hydrogen flow to obtain an LOI of the catalyst of about 2-4 wt % (the LOI of the catalyst is defined as the catalyst's weight loss after heating for two hours at 600° C.).

The hydrogen stream was stopped with the attaining of the reaction temperature. Isobutane containing about 2.5-3 wt % alkylate (added to accelerate deactivation rate, composition of the alkylate added is similar to alkylate produced by the process at the conditions described) and about 1 mol % of dissolved hydrogen was supplied to the reactor at a rate of about 4.0 kg/hour. About 95-98% of the isobutane/alkylate mixture was fed back to the reactor. About 2-5% was drained off for analysis. Such an amount of isobutane/alkylate mixture was supplied to the reactor as to ensure a constant quantity of liquid in the system. When the system had stabilized, hydrogen addition was stopped and such an amount of cis-2-butene was added to it as to give a cis-2-butene-WHSV of 0.16 or higher. The overall rate of flow of liquid in the system was maintained at about 4.0 kg/h. The weight ratio of isobutane to cis-2-butene at the reactor inlet was about 500-650. The pressure in the reactor amounted to about 21 bar. Total alkylate concentration of the hydrocarbon recycle flow (from added and produced alkylate) was maintained at about 6.5-7.5 wt % during the test by controlling the drain off flow to analyses.

Each time after 1 hour of reaction, the catalyst was regenerated by being washed with isobutane/alkylate mixture for 5 minutes, followed by 50 minutes of regeneration through being contacted with a solution of 1 mole % of H2 in isobutane/alkylate mixture, and then being washed with isobutane/alkylate mixture for another 5 minutes (total washing and regeneration time 1 hour). After this washing step, alkylation was started again.

The temperature during the washing steps, the regeneration step, and the reaction step was the same.

The process was conducted as above and the catalytic performance was measured as a function of time.

The performance was characterized by the olefin conversion per reactor pass and the research octane number (RON). The RON was determined as described on pages 13 and 14 of WO 9823560, the only exception being that the RON contribution of total C9+ (excl. 2,2,5-trimethylhexane) was estimated to be 84 instead of 90.

Olefin conversion per reactor pass is the weight fraction (as a percentage) of olefins that is converted between the inlet—and the outlet of the catalyst bed, not counting isomerization within the olefin molecules.

FIGS. 1, 2 and 3 shows the results of accelerated deactivation tests of the catalysts.

FIG. 1 shows that at the same test conditions (whsv=0.16) the new catalysts (with various amounts of RE on zeolite) maintains a higher conversion level of olefins than the reference (no RE) catalyst. FIG. 2 shows that the new catalysts permits a higher whsv (0.20) with similar deactivation rates compared to the reference catalyst. Thus, the new catalysts can be operated at higher whsv and accordingly less catalyst is required to produce a fixed quantity of alkylate, i.e., less catalyst is required at constant capacity of an alkylation plant. FIG. 3 shows that the new catalysts produce alkylate with at least the same RON as is obtained with the reference catalyst. The catalyst with about 5 wt % RE on zeolite combines the highest stability with a relatively high RON of alkylate produced.

The invention claimed is:

1. A process for alkylating hydrocarbons wherein an alkylatable organic compound comprising isobutane is reacted with an alkylation agent comprising butenes or a mixture of butenes to form an alkylate in the presence of a catalyst comprising Y zeolite, a hydrogenating function metal comprising platinum, palladium, or a mixture thereof, and a rare-earth containing solid acid constituent, with the catalyst being subjected intermittently to a regeneration step by being contacted with a feed containing a saturated hydrocarbon and hydrogen, said regeneration being carried out at 90% or less of the active cycle of the catalyst, with the active cycle of the catalyst being defined as the time from the start of the feeding of the alkylation agent to the moment when, in comparison with the entrance of the catalyst-containing reactor section, 20% of the alkylation agent leaves the catalyst-containing reactor section without being converted, not counting isomerization inside the molecule, wherein said catalyst is regenerated before there is any substantial decrease of activity of said catalyst.

2. The process of claim 1 wherein the regeneration is carried out at 60% or less of the active cycle of the catalyst.

3. The process of claim 2, wherein the regeneration is carried out at 20% or less of the active cycle of the catalyst.

4. The process of claim 1 wherein the catalyst has a particle diameter ranging from about 0.75 to about 2 mm.

5. The process of claim 1 wherein the catalyst comprises said hydrogenation function on a carrier comprising 2-98 wt. % of matrix material and the balance solid acid constituent.

6. The process of claim 5 wherein the catalyst carrier comprises 20-80 wt. % of matrix material and the balance solid acid constituent.

7. The process of claim 6, wherein the catalyst carrier comprises 20-50 wt. % of matrix material and the balance solid acid constituent.

8. The process of claim 5 wherein the matrix material comprises alumina.

9. The process of claim 1 wherein the solid acid constituent is prepared by a process comprising the steps of: preparing a sodium zeolite, ion exchanging the sodium zeolite with $NH_4^+$- and/or rare earth ions to reduce $Na_2O$ to about 3-6 wt %, steaming the zeolite at about 400 to about 500° C. such that a unit cell size ranges from about 24.56 to about 24.72 Å, ion exchanging with $NH_4^+$ ions to reduce $Na_2O$ to below about 1.5 wt %, and drying.

10. The process of claim 1 wherein the solid acid constituent is prepared by a process comprising the steps of: preparing a sodium zeolite, ion exchanging the sodium zeolite with $NH_4^+$- and/or rare earth ions to reduce $Na_2O$ to about 3.5-4.5 wt %, steaming the zeolite at about 400 to about 500° C. such that a unit cell size ranges from about 24.58 to about 24.68 Å, ion exchanging with $NH_4^+$ ions to reduce $Na_2O$ to below about 1.0 wt %, and drying.

11. The process of claim 1 wherein the solid acid constituent is prepared by a process comprising the steps of: preparing a sodium zeolite, ion exchanging the sodium zeolite with $NH_4^+$- and/or rare earth ions to reduce $Na_2O$ to about 3.5-4.5 wt %, steaming the zeolite at about 400 to about 500° C. such that a unit cell size ranges from about 24.60 to about 24.66 Å, ion exchanging with $NH_4^+$ ions to reduce $Na_2O$ to below about 0.7 wt %, and drying.

12. The process of claim 1 wherein the hydrogenation function metal is present in an amount of 0.01-2 wt. %, calculated as metal.

13. The process of claim 1 wherein the rare earth is lanthanum.

14. The process of claim 1 wherein the saturated hydrocarbon employed in the regeneration is the alkylatable organic compound.

15. The process of claim 14, wherein the regeneration temperature and/or the regeneration pressure do not differ by more than 50% from the reaction temperature, expressed in Celsius, and the reaction pressure, respectively.

16. The process of claim 15 wherein the regeneration temperature and/or the regeneration pressure do not differ by more than 20% from the reaction temperature, expressed in Celsius, and the reaction pressure, respectively.

17. The process of claim 16, wherein the regeneration is carried out at substantially the same temperature and/or pressure as the reaction.

18. The process of claim 1 wherein the length of the regeneration step is 0.1 to 10 times as long as the length of the reaction step.

19. The process of claim 18 wherein the length of the regeneration step is 0.5-2 times as long as the length of the reaction step.

20. The process of claim 1 wherein the regeneration step, is preceded by a washing step with a saturated hydrocarbon essentially in the absence of hydrogen and alkylation agent, is followed by a washing step with a saturated hydrocarbon essentially in the absence of hydrogen and alkylation agent, or both.

21. The process of claim 1 wherein the catalyst is periodically subjected to a high temperature regeneration with hydrogen in the gas phase.

22. The process of claim 21 wherein the catalyst is subjected to a high temperature regeneration with hydrogen in the gas phase after every 50 regenerations with saturated hydrocarbon and hydrogen.

23. The process of claim 1 wherein the catalyst is prepared by a) calcining solid acid-containing particles at a temperature in the range of 400-575° C., b) incorporating a hydrogenating function metal into the calcined particles to form hydrogenating function metal-containing particles, and c) calcining the hydrogenating function metal-containing particles at a temperature in the range of 350-600° C.

24. A process according to claim 23 wherein the temperature applied in step a) is in the range of 450-550° C.

25. A process according to claim 24 wherein the temperature is in the range of 460-500° C.

26. A process according to claim 25 wherein the temperature applied in step c) is in the range of 400-550° C.

27. A process according to claim 26 wherein the temperature is in the range of 450-500° C.

28. The process according to claim 1 wherein the catalyst further comprises from about 1.5 to about 6 wt % of water, measured as the loss on ignition at 600° C.

29. The process according to claim 28 wherein the catalyst comprises from about 1.8 to about 4 wt % of water.

30. The process according to claim 29 wherein the catalyst comprises from about 2 to about 3 wt % of water.

31. The process according to claim 28 wherein the catalyst is prepared by adding water to a dry catalyst comprising solid acid and hydrogenation metal before use in the alkylation process.

32. The process according to claim 28 wherein the alkylation process is started using a catalyst comprising less than about 1.5 wt % water and wherein water is added to the catalyst during the alkylation process.

* * * * *